United States Patent [19]

Morita

[11] Patent Number: 5,206,437
[45] Date of Patent: Apr. 27, 1993

[54] CALIXARENE DERIVATIVES AND PROCESSES FOR PRODUCTION THEREOF

[76] Inventor: Yutaka Morita, 101, Heights US, 2-52, Yamanoshita, Kamiueno-cho, Kyoto-fu, Mukou-shi, Japan

[21] Appl. No.: 592,546

[22] Filed: Oct. 2, 1990

[30] Foreign Application Priority Data

Oct. 2, 1989 [JP] Japan .................................. 1-257331

[51] Int. Cl.$^5$ ........................................... C07C 243/22
[52] U.S. Cl. ...................................... 564/310; 564/311
[58] Field of Search ....................... 549/354; 528/165; 525/504; 564/310, 311

[56] References Cited

U.S. PATENT DOCUMENTS 4,855,461  8/1989  Harris .................................. 549/354

FOREIGN PATENT DOCUMENTS 0279521  8/1988  European Pat. Off. ............. 549/354
0309291  3/1989  European Pat. Off. ............. 549/354

*Primary Examiner*—C. Warren Ivy
*Assistant Examiner*—Raymond Covington
*Attorney, Agent, or Firm*—Wenderoth, Lind & Ponack

[57] ABSTRACT

The present invention relates to novel calixarene derivatives having an inclusion activity which are useful for selective transportation of various metal ions, possess a biological activity and a redox activity, and are not only capable of forming conductive or photoconductive electron transfer complexes but also have strong ability of forming complexes and absorbing UV rays. The present invention also relates to intermediates of calixarene derivatives as well as processes for production thereof.

2 Claims, No Drawings

CALIXARENE DERIVATIVES AND PROCESSES FOR PRODUCTION THEREOF

BACKGROUND OF THE INVENTION

1. Field of the Invention

The present invention relates to novel calixarene derivatives having an inclusion activity which are useful for selective transportation of various metal ions, possess a biological activity and a redox activity, and are not only capable of forming conductive or photoconductive electron transfer complexes but also have strong ability of forming complexes and absorbing UV rays. The present invention also relates to intermediates of calixarene derivatives as well as processes for production thereof.

2. Description of the Prior Art

Calixarene derivatives represented by general formula [XV]:

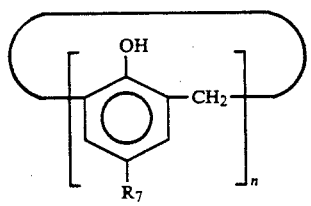

(wherein n represents an integer of 3 to 8; and $R_7$ represents a hydrogen atom, an alkyl group or a halogen atom) are metacyclophanes prepared by condensation and cyclization with formalin or paraformaldehyde and phenol derivatives having substituents such as an alkyl group, a halogen atom, etc., generally at the para position. While 5- or 7-mers are also known, 3, 4, 6 and 8-mers are conventional.

However, the calixarene derivatives described above and calixarene into which water-soluble groups such as a sulfone group, carboxyl group, etc. have been further introduced have simply an inclusion activity or a mere ability of selective transportation of metal ions, in terms of function. It was thus difficult to apply there derivatives to other areas than those described above.

The present inventor previously proposed in Japanese Patent Application No. 63-164716 calixarene derivatives which are useful for selective transportation of various metal ions, possess biological activity and redox activity, and are capable of forming conductive or photoconductive electron transfer complexes.

SUMMARY OF THE INVENTION

An object of the present invention is to provide novel calixarene derivatives having more improved properties possessed by the calixarene derivatives disclosed in Japanese Patent Application No. 63-164716 and further having new high abilities of forming complexes and absorbing UV rays, and intermediates thereof as well as processes for producing the calixarene derivatives described above.

Compounds represented by general formula [XII]:

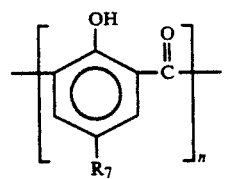

(wherein n represents an integer of 3 to 8; and $R_7$ represents a hydrogen atom, an alkyl group or a halogen atom) are those in which a methylene group in the calixarene derivatives is oxidized and converted to a carbonyl group; these compounds are called calixareone derivatives. The present invention is directed to calixarene derivatives represented by general formulae [I] and [II]:

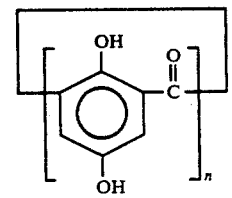

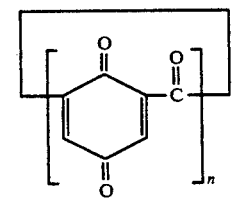

(wherein n represents an integer of 3 to 8); and processes for producing the same; as well as to calixareone derivatives represented by general formula [XVI]:

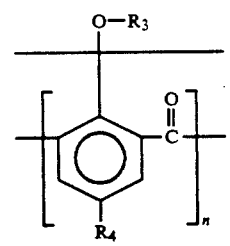

[wherein n represents an integer of 3 to 8; $R_3$ represents a hydrogen atoms or —$COR_5$ (wherein $R_5$ represents an alkyl group); $R_4$ represents —$OCOR_6$, —$NHCOR_6$ (wherein $R_6$ represents an alkyl group), —N=N—$R_2$ (wherein $R_2$ represents a phenyl group which may optionally have a substituent, a naphthyl group which may optionally have a substituent or a heterocyclic group which may optionally have a substituent), —$NH_2$, a halogen atom or an alkyl group (provided that when $R_3$ is a hydrogen atom or —$COCH_3$ and $R_4$ is tertiary butyl group, n is not 6)], which are intermediates of the compounds represented by general formulae [I] and [II].

During the course of extensive studies on calixarene derivatives, which were known to have only an inclusion activity and a selective transportation ability of metal ions, with an attempt to find additional new functions and effects, it has been found that the compounds represented by general formulae [I] and [II] are useful not only as having an inclusion activity but also for selective transportation of various metal ions, exhibit a biological activity and redox activity, and are not only capable of forming conductive or photoconductive electron transfer complexes but also have strong ability of forming complexes and absorbing UV rays. The present invention has thus been accomplished.

DETAILED DESCRIPTION OF PREFERRED EMBODIMENTS

In the compounds in accordance with the present invention which are represented by general formulae [I] and [II], n represents an integer of 3 to 8. In the compounds represented by general formula [XVI], n represents an integer of 3 to 8; $R_3$ represents a hydrogen atom or —$COR_5$ [wherein $R_5$ represents an alkyl group such as methyl group, ethyl group, propyl group, butyl group, amyl group, hexyl group, etc. (which may be a straight or branched chain)]; $R_4$ represents —$OCOR_6$, —$NHCOR_6$ (wherein $R_6$ represents the same alkyl group shown for $R_5$), —N=N—$R_2$ [wherein $R_2$ represents phenyl group, a phenyl group which has a substituent (examples of the substituent include a straight or branched chain alkyl group such as methyl group, ethyl group, propyl group, butyl group, amyl group, hexyl group, etc.; an alkoxy group such as methoxy group, ethoxy group, propoxy group, butoxy group, etc.; sulfone group, carboxyl group, a halogen atom such as iodine, bromine, chlorine, etc.), naphthyl group, a naphthyl group which has a substituent (examples of the substituent include a straight or branched chain alkyl group such as methyl group, ethyl group, propyl group, butyl group, amyl group, hexyl group, etc.; an alkoxy group such as methoxy group, ethoxy group, propoxy group, buytoxy group, etc.; sulfone group, carboxyl group, a halogen atom such as iodine, bromine, chlorine, etc.), a heterocyclic group (which is exemplified by pyridyl group, thiazole group, benzothiazole group, oxazole group, benzoxazole group, imidazole group, benzimidazole group, etc.), a heterocyclic group which has a substituent, (for example, a lower alkyl group such as methyl group, ethyl group, etc.; an alkoxy group such as methoxy group, ethoxy group, etc.; a halogen atom such as iodine, bromine, chlorine, etc.)] —$NH_2$, a halogen atom such as bromine, chlorine, etc., or an alkyl group (provided that when $R_3$ is a hydrogen atom or —$COCH_3$ and $R_4$ is tertiary butyl group, n is not 6).

The compounds in accordance with the present invention which are represented by general formulae [I], [II] and [XVI] can be synthesized, for example, by the following routes.

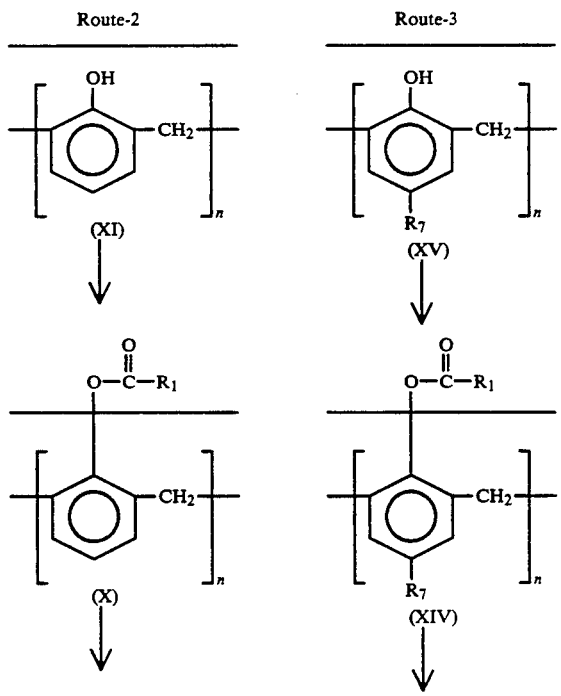

-continued
Route for Synthesis
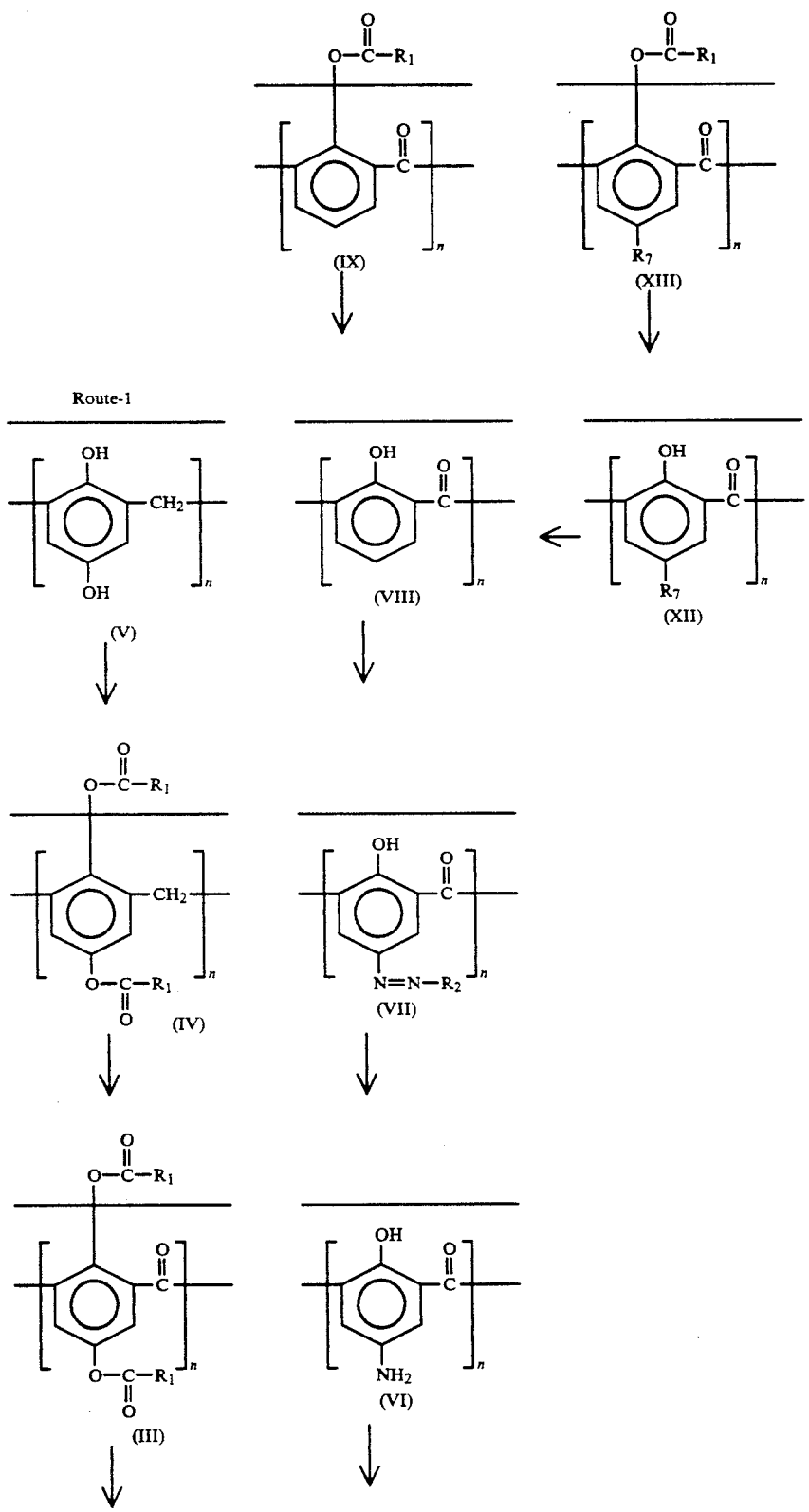

Route for Synthesis

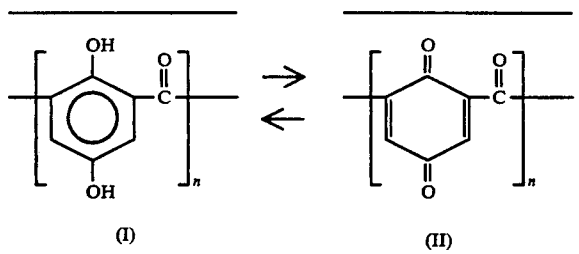

Route 1

The compound represented by general formula [III] can be obtained by oxidizing the compound represented by general formula [IV] in an organic solvent with an oxidizing agent such as ferric salts, nitrates, bichromates, peroxides, etc. The compound of formula [III] is hydrolyzed under basic or acidic conditions to give the compound represented by general formula [I].

The compound represented by general formula [IV] can be readily synthesized by reacting the compound represented by general formula [V] with an acylating agent such as acetic anhydride, an acyl chloride, etc. in a conventional manner. The compound represented by general formula [V] can be synthesized by the process disclosed in Japanese Patent Application No. 63-164716.

Route 2

The compound represented by general formula [IX] can be obtained by oxidizing the compound represented by general formula [X] in an organic solvent with an oxidizing agent such as ferric salts, nitrates, bichromates, peroxides, etc. The compound of formula [IX] is hydrolyzed under basic or acidic conditions to give the compound represented by general formula [VIII]. Coupling of the compound of formula [VIII] with a diazonium salt of an aromatic or heterocyclic compound gives the compound represented by general formula [VII]. When the compound of formula [VII] is reacted with a conventional reducing agent, e.g., hydrosulfite, tin chloride, etc., the compound represented by general formula [VI] can be obtained.

The compound represented by general formula [II] can be obtained by oxidizing the compound represented by general formula [VI] in an organic solvent with an oxidizing agent such as ferric salts, nitrates, bichromates, peroxides, etc.

The compound represented by general formula [X] described above can be readily synthesized by reacting the compound represented by general formula [XI] with an acylating agent such as acetic anhydride, an acyl chloride, etc. in a conventional manner. The aromatic diazonium salt which can be used in the present invention can be obtained by reacting an aromatic amine which may optionally be substituted, such as an aniline, a sulfanilic acid, a p-aminobenzoic acid, a naphthylamine, a sulfonaphthylamine, etc., with nitric acid. The diazonium salt of the heterocyclic compound may be readily obtained by reacting a heterocyclic compound which may optionally be substituted, such as an aminopyridine, an aminothiazole, an aminoxazole, a benzoxazole, an aminoimidazole, an aminobenzoxazole, etc., with nitric acid.

The compounds of general formulae [I] and [II] are compounds of mutual oxidation and reduction type and may easily be converted to each other. That is, when the compound represented by general formula [I] is oxidized with an oxidizing agent such as a ferric salt, a ferricyanide, a bichromate, a peroxide, etc., the compound represented by general formula [II] can be obtained, when the compound represented by general formula [II] is reduced with a conventional reducing agent such as hydrosulfite, tin chloride, a sulfite, etc., the compound represented by general formula [I] can be obtained.

Route 3

When the calixarene derivatives represented by general formula [XV] is acetylated in a conventional manner, the compound represented by general formula [XIV] can be obtained. The compound of formula [XIV] is oxidized with an oxidizing agent such as ferric salts, nitrates, bichromates, peroxides, etc. in an organic solvent to give the compound represented by general formula [XIII]. The compound of formula [XIII] is hydrolyzed under basic or acidic conditions to give the compound represented by general formula [XII].

The compound of formula [XII] is reacted with a Friedel-Crafts catalyst such as anhydrous aluminum chloride, etc. in an organic solvent to eliminate the substituent, whereby the compound represented by general formula [VIII] can be obtained.

Following [Route 2], the compound represented by general formula [II] can then be obtained.

Next, the present invention is described in more detail with reference to the examples but is not deemed to be limited to these examples.

EXAMPLES

Example 1

Synthesis of p-hydroquinone type calix[4]areone (Compound of general formula [I] wherein n is 4) by [Route 1]

(1) Synthesis of p-acetoxy-acetoxycalix[4]arene (Compound of general formula [III] wherein n is 4 and $R_1$ is methyl)

To 1.22 g of p-hydroxy-hydroxycalix[4]areone (Compound of general formula [V] wherein n is 4) were added 20 ml of acetic anhydride and one drop of conc. sulfuric acid. After the mixture was refluxed for 2 hours, it was cooled to 20° C. While stirring, a solution of 1.6 g of chromic anhydride in 15 ml of acetic anhydride and 5 ml of acetic acid was dropwise added to the mixture. The mixture was reacted at 20° C. for 2 hours. Then, the temperature was elevated to 45° C. After reacting for 4 hours at 45° C., the temperature was further elevated to reflux for 2 hours. After cooling, 200 ml of ice water was added to the reaction mixture. The formed precipitates were collected by filtration, washed with water and recrystallized from acetone to give 1.6 g of p-acetoxyacetoxycalix[4]areone as white crystals.

Melting point: 359° C.

Elemental analysis $(C_{11}H_8O_5)_4$, molecular weight 880.73 Calcd. (%): C; 60.00 H; 3.66. Found: (%): C; 59.62 H; 4.11.

IR: $(KBr)cm^{-1}$: 3100 $(CH_3)$, 1770 $(C=O)$, 1670 $(C=O)$, 1590 (benzene ring), 900 (benzene ring), 1200–1150 $(C=O)$.

(2) Synthesis of p-hydroquinone type calix[4]areone (Compound of general formula [I] wherein n is 4)

In 40 cc of dioxan was dissolved 1 g of p-acetoxy-acetoxycalix[4]areone obtained in (1). The solution was then added to 20 ml of 10% sodium hydroxide aqueous solution. The mixture was stirred at 45° C. for 2 hours in nitrogen flow to perform hydrolysis. The mixture was neutralized with 1% hydrochloric acid to adjust the pH to 2–3, whereby light yellow precipitates were formed. The precipitates were collected by filtration and washed with water. Since the precipitates were insoluble in almost all organic solvents, they were dissolved in 10% sodium hydroxide aqueous solution. The solution was neutralized with 1% hydrochloric acid. By repeating reprecipitation 2 to 3 times, the precipitates were purified to give 0.6 g of light yellow p-hydroquinone type calix[4]areone as crystalline powders.

Decomposition point; decomposed at 250° C. or higher.

Elemental analysis $(C_7H_4O_3)_4$, molecular weight 544.43 Calcd. (%): C; 61.77 H; 2.96. Found (%): C; 61.18 H; 3.45.

IR: $(KBr)cm^{-1}$ 3500–3000 (OH), 1615 $(C=O)$.

(3) Synthesis of p-benzoquinone type calix[4]areone (Compound of general formula [II] wherein n is 4)

In 30 ml of acetic acid was dispersed 1.33 g of p-hydroxy-hydroxycalix[4]areone obtained in (2). A solution of 4.9 g of anhydrous iron chloride in 10 ml of water and 10 ml of conc. hydrochloric acid was dropwise added to the dispersion. The mixture was stirred at 50° C. for 2 hours to form reddish brown precipitates. The precipitates were collected filtration, washed with water and recrystallized form acetone to give 0.37 g of p-benzoquinone type calix[4]areone as reddish brown crystalline powders.

Decomposition point: decomposed at 250° C.

Elemental analysis $(C_7H_2O_3)_4$, molecular weight 536.4 Calcd. (%): C; 62.70 H; 1.50. Found (%): C; 62.28 H; 2.22.

IR: $(KBr)cm^{-1}$
1660 $(C=O)$, 1600 (benzene ring), 1300 $(C=O)$.

Example 2

Synthesis of p-hydroquinone type calix [4]areone (Compound of general formula [I] wherein n is 40 by [Route 2]

(1) Synthesis of acetoxy-calix[4]areone (Compound of general formula [IX] wherein n is 4 and $R_1$ is methyl)

To 1.22 g of calix[4]arene (Compound of general formula [XI] wherein n is 4) were added 20 ml of acetic anhydride and one drop of conc. sulfuric acid. After the mixture was refluxed for 2 hours, it was cooled to 20° C. While stirring, a solution of 1.6 g of chromic anhydride in 15 ml of acetic anhydride and 5 ml of acetic acid was dropwise added to the mixture. The mixture was reacted at 20° C. for 2 hours. Then, the temperature was elevated to 45° C. After reacting for 4 hours at 45° C., the temperature was further elevated to reflux for 2 hours. After cooling, 200 ml of ice water was added to the reaction mixture. The formed precipitates were collected by filtration, washed with water and recrystallized from methanol to give 1.6 g of acetoxycalix[4]areone as white crystals. Melting point: 368° C.

Elemental analysis $(C_9H_6O_3)_4$, molecular weight 648.58 Calcd. (%): C; 66.67 H; 3.73. Found (%): C; 66.14 H; 4.31.

IR: $(KBr)cm^{-1}$ 1760 $(C=O)$, 1670 $(C=O)$, 1595 (benzene ring).

(2) Synthesis of calix[4]areone (Compound of general formula [VIII] wherein n is 4)

After 4.8 g of acetoxycalix[4]areone synthesized in (1) was dissolved in 190 ml of dioxan, 100 ml of 10% sodium hydroxide aqueous solution was added to the solution. The mixture as refluxed for 2 hours in a nitrogen flow to cause hydrolysis. The mixture was neutralized with 1% hydrochloric acid to adjust the pH of 2–3, whereby white precipitates were formed. The precipitates were collected by filtration, washed with water and recrystallized from acetone to give 2.91 g of calix[4]areone as white crystalline powders.

Melting point: 261° C.

Elemental analysis $(C_7H_4O_2)_4$, molecular weight 480.43 Calcd. (%): C; 70.00 H; 3.36. Found (%): C; 69.64 H; 3.83.

IR: $(KBr)cm^{-1}$ 3200 (OH), 1650 $(C=O)$, 1595 (benzene ring).

(3) Synthesis of p-carboxybenzene-azo-hydroxycalix[4]areone (Compound of general formula [VII] wherein n is 4 and $R_2$ is phenylcarboxy)

A solution of benzoic acid diazonium chloride was prepared from 1.51 g of p-aminobenzoic acid, 23.7 ml of water, 3.4 g of 36% hydrochloric acid and 0.84 g of sodium nitrite in a conventional manner. After 1g of calix[4]areone was dissolved in 15 ml of DMF, 10 ml of methanol and 9.4 g of sodium acetate, the solution was cooled to 5° C. Then, the diazonium chloride solution described above was dropwise added to the solution. After the dropwise addition, the mixture was stirred for 2 hours. Then, 150 ml of water and 1 ml of conc. hydrochloric acid were added followed by stirring at 90° C. for an hour. The precipitates were filtered and washed with water. After neutralizing with 1% hydrochloric acid, the precipitates were again precipitated for purification. Thus, 0.76 g of p-carboxybenzene-azo-hydroxycalix[4]areone was obtained as red crystalline powders.

Decomposition point: decomposed at 280° C.

Elemental analysis $(C_{14}H_8O_4N_2)_4$, molecular weight 1072. Calcd. (%): C; 62.69 H; 3.01 N; 10.44 Found (%): C; 62.17 H; 3.53 N; 10.93.

IR: $(KBr)cm^{-1}$ 3599–2500 (OH.COOH), 1690 $(C=O)$, 1645 $(C=O)$, 1595 (benzene ring), 1420 (OH).

(4) Synthesis of p-amino-hydroxycalix[4]areone (Compound of general formula [VI] wherein n is 4)

In 50 ml of 5% sodium hydroxide aqueous solution was dissolved 2.7 g of p-carboxybenzeneazo-hydroxycalix[4]areone obtained in (3). After the solution was heated to 80° C. 7 g of hydrosulfite was added to the solution. The mixture was stirred for an hour to cause decoloration and then form light yellow brown precipitates. The precipitates were filtered, washed with water and recrystallized from methanol to give 0.9 g of p- amino-hydrocalix[4]areone as light yellow brown crystalline powders.

Melting point: 170° C.

Elemental analysis $(C_7H_5O_2N_1)_4$, molecular weight 540.49 Calcd. (%): C; 62.22 H; 3.73 N; 10.37. Found (%): C; 61.74 H; 4.11 N; 10.89.

IR: $(KBr)cm^{-1}$ 3350-3200 (OH), 3100-2700 ($NH_2$), 1660 (C=O), 1620 (benzene ring).

(5) Synthesis of p-benzoquinone type calix[4]areone (Compound of general formula [II] wherein n is 4)

After 1.34 g of p-amino-hydroxycalix[4]areone obtained in (4) was dissolved in 100 ml of 1% hydrochloric acid, a solution of 4.9 g of anhydrous iron chloride in 10 ml of water and 10 ml of conc. hydrochloric acid was dropwise added to the solution. The mixture was stirred for 2 hours to form red brown precipitates. The precipitates were collected by filtration, washed with water and recrystallized from acetone to give 0.7 g of p-benzoquinone type calix[4]areone as red brown crystalline powders.

(6) Synthesis of p-hydroxy-hydroxycalix[4]areone (Compound of general formula [I] wherein n is 4)

After 1.34 g of p-benzoquinone type calix[4]areone obtained in (5) was dissolved in 100 ml of 5% sodium hydroxide aqueous solution, 7 g of hydrosulfite was added to the solution. The mixture was stirred at 70° C. for an hour and then neutralized with 1% hydrochloric acid to give 0.42 g of light yellow p-hydroxy-hydroxycalix[4]areone.

Example 3

Synthesis of p-hydroquinone type calix[4]areone (Compound of general formula [I] wherein n is 4) by [Router 3]

(1) Synthesis of p-tertiary-octyl-acetoxy-calix[4]areone (Compound of general formula [XIII] wherein n is 4, $R_7$ is tertiary octyl and $R_1$ is methyl)

To 6.5 g of p-tertiary-octyl-hydroxycalix[4]arene (Compound of general formula [XV] wherein n is 4 and $R_7$ is tertiary octyl) were added 20 ml of acetic anhydride and one drop of conc. sulfuric acid. After the mixture was refluxed for 2 hours, it was cooled to 20° C. While stirring, a solution of 1.6 g of chromic anhydride in 15 ml of acetic anhydride and 5 ml of acetic acid was dropwise added to the mixture. The mixture was reacted at 20° C. for 2 hours. Then, the temperature was elevated to 45° C. After reacting for 4 hours at 45° C., the temperature was further elevated to reflux for 2 hours. After cooling, 200 ml of ice water was added to the reaction mixture. The formed precipitates were collected by filtration, washed with water and recrystallized rom acetone to give 7.9 g of p-tertiary-octyl-acetoxycalix[4]areone as white crystals.

Melting point: 255° C.

Elemental analysis $(C_{17}H_{22}O_3)_4$, molecular 1097.44 Calcd. (%): C; 74.42 H; 8.08. Found (%): C; 73.91 H; 8.49.

IR: $(KBr)cm^{-1}$ 2900 (methylene), 1770 (C=O), 1665 (C=O), 1390; 1370 (tertiary octyl).

(2) Synthesis of p-tertiary-octyl-hydroxycalix[4]areone (Compound of general formula [XII] wherein n is 4 and $R_7$ is tertiary-octyl After 1 g of p-tertiary-octyl-acetoxycalix[4]areone obtained in (1) was dissolved in 40 ml of dioxan, 20 ml of 10% sodium hydroxide aqueous solution was added to the solution. The mixture as refluxed for 2 hours in a nitrogen flow to cause hydrolysis. The mixture was neutralized with 1% hydrochloric acid to adjust the pH to 2-3, whereby white precipitates were formed. The precipitates were collected by filtration, washed with eater and recrystallized form acetone to give 0.78 g of p-tertiary-octyl-hydroxycalix[4]-areone as white crystalline powders.

Melting point: 258° C.

Elemental analysis $(C_{15}H_{20}O_2)_4$, molecular weight 929.24 Calcd. (%): C; 77.55 H; 8.68. Found (%): C; 77.08 H; 9.13.

IR: $(KBr)cm^{-1}$ 3490 (OH), 1650 (C=O), 1390; 1370 (tertiary octyl).

(3) Synthesis of p-hydroxycalix[4]areone (Compound of general formula [VIII] wherein n is 4)

After 4.6 g of p-tertiary-octyl-hydroxycalix[4]areone obtained in (2) was dispersed in 80 ml of absolute toluene, 3.8 g of anhydrous aluminum chloride was gradually added to the dispersion at room temperature. The mixture was then stirred for 4 hours. After 40 ml of 10% hydrochloric acid cooled to 0° C. was added to the mixture, the toluene layer was taken by a separatory funnel and washed with water. Toluene was then evaporated off with a rotary evaporator. The resulting solid was washed with ether and recrystallized from chloroform to give 1.68 g of hydroxycalix[4]areone as white crystalline powders.

The compound was identical with the compound obtained in Example 2 (2), indicating that p-hydroquinone type calix[4]areone was obtained by the same route.

What is claimed is:

1. A calixarene derivative represented by formula [I] of formula [II]:

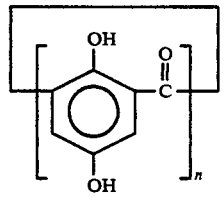

[I]

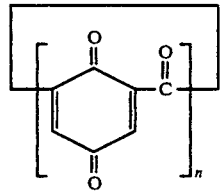

[II]

wherein n represents an integer of 3 to 8.

2. A calixarene derivative represented by formula [XVI]:

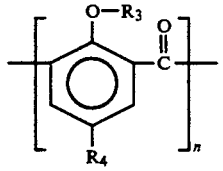

[XVI]

wherein n represents an integer of 3 to 8; $R_3$ represents a hydrogen atom or —$COR_5$ wherein $R_5$ represents an alkyl group; and $R_4$ represents —N=N—$R_2$ wherein $R_2$ represents a phenyl group which may optionally be substituted or a naphthyl group which may optionally be substituted wherein the substituents for the phenyl and naphthyl groups are selected from the group consisting of straight or branched chain alkyl, alkoxy, sulfone, carboxyl and halogen.

* * * * *